United States Patent
Richter et al.

(10) Patent No.: US 10,487,377 B2
(45) Date of Patent: Nov. 26, 2019

(54) CR, NI, MO AND CO ALLOY FOR USE IN MEDICAL DEVICES

(71) Applicants: Heraeus Deutschland GmbH & Co. KG, Hanau (DE); Saes Smart Materials, Inc., New Hartford, NY (US)

(72) Inventors: René Richter, Babenhausen (DE); Jörg-Martin Gebert, Karlsruhe (DE); Heiko Specht, Hanau (DE); Francis E. Sczerzenie, Lake Pleasant, NY (US); Radhakrishnan M. Manjeri, New Hartford, NY (US); Weimin Yin, Ridgefield, CT (US)

(73) Assignees: Heraeus Deutschland GmbH & Co. KG, Hanua (DE); Saes Smart Materials, Inc., New Hartford, NY (US)

( * ) Notice: Subject to any disclaimer, the term of this patent is extended or adjusted under 35 U.S.C. 154(b) by 123 days.

(21) Appl. No.: 15/382,294

(22) Filed: Dec. 16, 2016

(65) Prior Publication Data
US 2017/0175235 A1    Jun. 22, 2017

Related U.S. Application Data

(60) Provisional application No. 62/269,268, filed on Dec. 18, 2015.

(51) Int. Cl.
*C22C 30/00* (2006.01)
*C22C 1/02* (2006.01)
(Continued)

(52) U.S. Cl.
CPC .............. *C22C 30/00* (2013.01); *A61N 1/056* (2013.01); *A61N 1/375* (2013.01); *C22C 1/02* (2013.01)

(58) Field of Classification Search
CPC .................................. C22C 30/00; C22C 1/02
See application file for complete search history.

(56) References Cited

U.S. PATENT DOCUMENTS 2,525,130 A * 10/1950 Hall .................. C22C 21/02
420/534
2,743,175 A * 4/1956 Talbot ................ C22C 30/00
420/453
(Continued)

FOREIGN PATENT DOCUMENTS

EP            1664360         3/2005
WO          2004006377        1/2004
(Continued)

OTHER PUBLICATIONS

ASTM International, "Standard Specification for Wrought 35Cobalt-35Nickel-20Chromium-10Molybdenum Alloy for Surgical Implant Applications (UNS R30035)," Designation: F562-13, pp. 5 (Mar. 1, 2013).
(Continued)

*Primary Examiner* — Cam N. Nguyen
(74) *Attorney, Agent, or Firm* — Dicke, Billig & Czaja, PLLC

(57) ABSTRACT

One aspect generally relates to a Cr, Ni, Mo and Co alloy, with tightly controlled levels of impurities. One aspect relates to an alloy including about 10 to about 30 weight % Cr, about 20 to about 50 weight % Ni, about 2 to about 20 weight % Mo, about 10 to about 50 weight % Co, and less than about 0.01 weight % Al, wherein each weight % is based on the total weight of the alloy.

10 Claims, 9 Drawing Sheets

(51) Int. Cl.
*A61N 1/375* (2006.01)
*A61N 1/05* (2006.01)

(56) References Cited

U.S. PATENT DOCUMENTS

| | | | | |
|---|---|---|---|---|
| 3,356,542 | A | 12/1967 | Smith | |
| 4,487,744 | A * | 12/1984 | DeBold | C22C 30/00 219/146.23 |
| 4,652,315 | A * | 3/1987 | Igarashi | C22C 30/00 148/410 |
| 5,077,006 | A * | 12/1991 | Culling | C22C 30/00 420/40 |
| 5,096,667 | A * | 3/1992 | Fetcenko | C01B 3/0031 420/580 |
| 5,104,607 | A * | 4/1992 | Driska | B29C 49/50 264/528 |
| 5,130,085 | A * | 7/1992 | Tendo | C22C 30/00 420/40 |
| 5,238,756 | A * | 8/1993 | Fetcenko | B82Y 30/00 420/900 |
| 5,283,032 | A * | 2/1994 | Wanner | C22C 19/05 420/586 |
| 5,403,547 | A * | 4/1995 | Smith | C22C 30/00 420/447 |
| 5,439,640 | A * | 8/1995 | Heck | C22C 30/00 420/585 |
| 5,478,417 | A * | 12/1995 | Heck | C22C 30/00 148/328 |
| 5,630,840 | A | 5/1997 | Mayer | |
| 5,939,204 | A * | 8/1999 | Czech | B32B 15/01 420/34 |
| 5,945,067 | A * | 8/1999 | Hibner | C21D 6/02 420/586 |
| 6,623,869 | B1 * | 9/2003 | Nishiyama | B32B 15/01 138/143 |
| 6,761,777 | B1 * | 7/2004 | Radon | C22C 30/00 148/324 |
| 7,015,392 | B1 | 3/2006 | Dickenson | |
| 7,280,875 | B1 | 10/2007 | Chitre | |
| 7,396,597 | B2 * | 7/2008 | Nishiyama | C22C 30/00 138/140 |
| 7,715,721 | B2 * | 5/2010 | Solheim | H04J 14/0283 398/175 |
| 7,758,805 | B2 * | 7/2010 | Kohno | C01B 3/0047 420/580 |
| 8,313,591 | B2 * | 11/2012 | Hirata | C21D 6/001 148/442 |
| 8,479,700 | B2 * | 7/2013 | Qiao | C22C 1/02 123/188.3 |
| 8,808,473 | B2 * | 8/2014 | Hirata | C22C 19/055 148/427 |
| 9,138,963 | B2 * | 9/2015 | Cetel | C22C 19/056 |
| 9,228,250 | B2 * | 1/2016 | Alves | B23K 35/0261 |
| 9,243,304 | B2 * | 1/2016 | Pieper | C21D 8/1222 |
| 9,260,770 | B2 * | 2/2016 | Jonsson | C22C 19/055 |
| 9,650,698 | B2 * | 5/2017 | Hattendorf | C22C 19/053 |
| 9,856,544 | B2 * | 1/2018 | Young | C22C 14/00 |
| 9,932,655 | B2 * | 4/2018 | Hamaguchi | C22C 30/00 |
| 10,109,855 | B2 * | 10/2018 | Young | H01M 4/385 |
| 2005/0051243 | A1 | 3/2005 | Forbes Jones et al. | |
| 2010/0075168 | A1 | 3/2010 | Schaffer | |
| 2016/0051384 | A1 | 2/2016 | Patel | |
| 2016/0111178 | A1 | 4/2016 | McIntyre | |
| 2017/0216494 | A1 | 8/2017 | Roth | |
| 2018/0192939 | A1 | 7/2018 | Roth | |
| 2018/0304042 | A1 | 10/2018 | Donegan | |

FOREIGN PATENT DOCUMENTS

| | | |
|---|---|---|
| WO | 2005026399 | 3/2005 |
| WO | 2016064790 | 4/2016 |

OTHER PUBLICATIONS

The Office Action for U.S. Appl. No. 151996,554 dated Jan. 10, 2019 (26 pgs.).

* cited by examiner

US 10,487,377 B2

CR, NI, MO AND CO ALLOY FOR USE IN MEDICAL DEVICES

CROSS REFERENCE TO RELATED APPLICATION

This Non-Provisional Patent Application claims the benefit of the filing date of U.S. Provisional Patent Application Ser. No. 62/269,268, filed Dec. 18, 2015, entitled "AN ALLOY COMPRISING CR, NI, MO AND CO FOR USE IN MEDICAL DEVICES," which is herein incorporated by reference.

This Patent Application is also related to Patent Application Ser. No. 62/519,719 filed on Jun. 14, 2017, entitled "COMPOSITE WIRE"; patent application Ser. No. 15/996,554 filed on Jun. 4, 2018, entitled "COMPOSITE WIRE"; Patent Application Ser. No. 62/519,749 filed on Jun. 14, 2017, entitled "METHOD FOR MANUFACTURING A COMPOSITE WIRE"; patent application Ser. No. 15/996,555 filed on Jun. 4, 2018, entitled "METHOD FOR MANUFACTURING A COMPOSITE WIRE"; Patent Application Ser. No. 62/519,779 filed on Jun. 14, 2017, entitled "METHOD FOR MANUFACTURING A CABLE"; patent application Ser. No. 15/996,557 filed on Jun. 4, 2018, entitled "METHOD FOR MANUFACTURING A CABLE"; Patent Application Ser. No. 62/519,823 filed on Jun. 14, 2017, entitled "METHOD FOR MANUFACTURING A PASSIVATED PRODUCT"; and patent application Ser. No. 15/996,558 filed on Jun. 4, 2018, entitled "METHOD FOR MANUFACTURING A PASSIVATED PRODUCT".

BACKGROUND

One aspect generally relates to a Cr, Ni, Mo and Co alloy, with tightly controlled levels of impurities. One aspect further relates to a process for the preparation of an alloy, an alloy obtainable therefrom, a lead, and the use of a lead in medical devices, such as pacemakers.

Much investigation in recent years has been directed to a search for new high performance alloys, such as for medical applications where a very high value is placed on reliability and materials are required which exhibit a low failure rate even over a long time period.

Cardiac Pacemakers, Implantable Cardioverter Defibrillation Devices and Cardiac Resynchronization Devices are applications where reliability is particularly important, especially in terms of resistance to physical fatigue and to chemical corrosion. Invasive surgery is required to implant a pacemaker into the body or remove or replace parts, and it is highly desirable for the individual components of the pacemaker to have a long working life in order to reduce the requirement for surgical intervention. Furthermore, it is desirable for the working life to have a low variance. In a heart pacemaker, one component which is exposed to a particularly high amount of stress during normal operation is the so called lead which connects the implantable pulse generator to the heart tissue. A flexible lead is required in order to connect the implantable pulse generator to the heart tissue without imposing undue physical stress on the heart and the lead flexes during normal operation, typically repetitively with a frequency on the order of that of a human heart beat. A high resistance to fatigue is therefore required in the lead in order to withstand frequent physical stress over a long period of time. A high resistance of the lead to corrosion is important not only in terms of the lifetime of the component, but also in terms of reducing toxicity to the body.

WO 2005026399 A1 discusses an approach to improving the properties of an alloy by reducing the content of titanium nitride and mixed metal carbonitride.

US 2005/0051243 A1 focuses on alloys with a reduced content of nitrogen.

There persists a requirement for alloys having improved performance, such as with regard to improving resistance to physical fatigue.

For these and other reasons, a need exists for the present invention.

SUMMARY

One aspect is generally based on the object of overcoming at least one of the problems encountered in the state of the art in relation to alloys.

More specifically, one aspect is further based on the object of providing an alloy having improved properties.

One embodiment provides an alloy that has improved resistance to physical fatigue, and also has a high corrosion resistance. One embodiment provides an alloy that can be drawn into a thin wire, such as less than about 50 μm.

One embodiment provides a method for the preparation of an alloy having improved properties, such as an improved resistance to physical fatigue, and also having a high corrosion resistance, and also which can be drawn into a thin wire, such as less than about 50 μm.

One embodiment provides a wire having comparable tensile properties to known wire, but for which the proportion of outlying failures in fatigue resistance is reduced.

A contribution to achieving at least one of the above described objects is made by the following embodiments.

1. An alloy comprising the following alloy components:
   a) Cr in the range from about 10 to about 30 weight %, in one embodiment in the range from about 15 to about 25 weight %, or in one embodiment in the range from about 19 to about 21 weight %;
   b) Ni in the range from about 20 to about 50 weight %, in one embodiment in the range from about 30 to about 45 weight %, or in one embodiment in the range from about 33 to about 37 weight %;
   c) Mo in the range from about 2 to about 20 weight %, in one embodiment in the range from about 5 to about 15 weight %, or in one embodiment in the range from about 9 to about 10.5 weight %;
   d) Co in the range from about 10 to about 50 weight %, in one embodiment in the range from about 20 to about 40 weight %, or in one embodiment in the range from about 33 to about 37 weight %;
   wherein the Al content of the alloy is less than about 0.01 weight %, in one embodiment less than about 0.005 weight %, or in one embodiment less than about 0.001 weight %;
   wherein each weight % is based on the total weight of the alloy.
2. The alloy according to embodiment 1, wherein the content of Mg is less than about 0.005 weight %, in one embodiment less than about 0.0001 weight %, or in one embodiment less than about 0.00001 weight %, based on the total weight of the alloy.
3. The alloy according to embodiment 1 or 2, wherein the content of Ca is less than about 0.005 weight %, in one embodiment less than about 0.0001 weight % or in one embodiment less than about 0.00001 weight %, based on the total weight of the alloy.
4. The alloy according to any of the preceding embodiments, wherein the content of Ce is less than about 0.005 weight %, in one embodiment less than about 0.0001 weight % or in one embodiment less than about 0.00001 weight %, based on the total weight of the alloy.

5. The alloy according to any of the preceding embodiments, wherein the content of Ti is less than about 0.1 weight %, in one embodiment less than about 0.01 weight % or in one embodiment less than about 0.001 weight %, further or in one embodiment less than about 0.0005 weight %, based on the total weight of the alloy.

6. The alloy according to any of the preceding embodiments, wherein the content of Fe is in the range from about 0.0001 to about 1 weight %, in one embodiment in the range from about 0.0005 to about 0.1 weight %, or in one embodiment in the range from about 0.001 to about 0.05 weight %, based on the total weight of the alloy.

7. The alloy according to any of the preceding embodiments, wherein at least one of the following is satisfied:
   a) The content of C in the alloy is less than about 0.1 weight %, in one embodiment less than about 0.08 weight % or in one embodiment less than about 0.05 weight %
   b) The content of B in the alloy is less than about 0.01 weight %, in one embodiment less than about 0.001 wt %, or in one embodiment less than about 0.0002 weight %;
   c) The content of P in the alloy is less than about 0.01 weight %, in one embodiment less than about 0.005 weight %, or in one embodiment less than about 0.001 weight %, further or in one embodiment less than about 0.0005 weight %;
   d) The content of S in the alloy is less than about 0.005 weight %, in one embodiment less than about 0.003 weight %, or in one embodiment less than about 0.002 weight %, further or in one embodiment less than about 0.0008 weight %;

each weight % being based on the total weight of the alloy. In preferred aspects of this embodiment, the combination of the above criteria which are satisfied is selected from the group consisting of: a), b), c), d), a)+b), a)+c), a)+d), b)+c), b)+d), c)+d), a)+b)+c), a)+b)+d), a)+c)+d), b)+c)+d) and a)+b)+c)+d).

8. The alloy according to any of the preceding embodiments, wherein at least one of the following is satisfied:
   a) The content of Mn in the alloy is less than about 0.05 weight %, in one embodiment less than about 0.005 weight %, or in one embodiment less than about 0.001 weight %;
   b) The content of Si in the alloy is less than about 0.05 weight %, in one embodiment less than about 0.03 weight %, or in one embodiment less than about 0.02 weight %;

each weight % being based on the total weight of the alloy. In preferred aspects of this embodiment, the combination of the above criteria which are satisfied is selected from the group consisting of: a), b), a)+b).

9. The alloy according to any of the preceding embodiments, wherein at least one of the following is satisfied:
   a) The content of O in the alloy is in the range from about 0.0001 to about 0.05 weight %, in one embodiment in the range from about 0.0001 to about 0.03 weight %, or in one embodiment in the range from about 0.0001 to about 0.01 weight %;
   b) The content of N in the alloy is in the range from about 0.0001 to about 0.01 weight %, in one embodiment in the range from about 0.0001 to about 0.008 weight %, or in one embodiment in the range from about 0.0001 to about 0.005 weight %;

each weight % being based on the total weight of the alloy. In preferred aspects of this embodiment, the combination of the above criteria which are satisfied is selected from the group consisting of: a), b), a)+b).

10. The alloy according to any of the preceding embodiments, wherein at least one of the following is satisfied:
    a) The alloy contains less than about 0.01 weight %, in one embodiment less than about 0.005 weight %, or in one embodiment less than about 0.001 weight %, O in the form of a magnesium oxide;
    b) The alloy contains less than about 0.01 weight %, in one embodiment less than about 0.005 weight %, or in one embodiment less than about 0.001 weight %, O in the form of an aluminium oxide;
    c) The alloy contains less than about 0.01 weight %, in one embodiment less than about 0.005 weight %, or in one embodiment less than about 0.001 weight %, O in the form of a cerium oxide.
    d) The alloy contains less than about 0.01 weight %, in one embodiment less than about 0.005 weight %, or in one embodiment less than about 0.001 weight %, O in the form of a calcium oxide.
    e) The alloy contains less than about 0.01 weight %, in one embodiment less than about 0.005 weight %, or in one embodiment less than about 0.001 weight %, O in the form of a chromium oxide.

In preferred aspects of this embodiment, the combination of the above criteria which are satisfied is selected from the group consisting of: a), b), c), d), a)+b), a)+c), a)+d), b)+c), b)+d), c)+d), a)+b)+c), a)+b)+d), a)+c)+d), b)+c)+d), a)+b)+c)+d), e), a)+e), b)+e), c)+e), d)+e), a)+b)+e), a)+c)+e), a)+d)+e), b)+c)+e), b)+d)+e), c)+d)+e), a)+b)+c)+e), a)+b)+d)+e), a)+c)+d)+e), b)+c)+d)+e) and a)+b)+c)+d)+e).

11. A process for the preparation of an alloy comprising the following preparation steps:
    a) Provision of a mixture comprising the following components:
       i. Cr in the range from about 10 to about 30 weight %, in one embodiment in the range from about 15 to about 25 weight %, or in one embodiment in the range from about 19 to about 21 weight %;
       ii. Ni in the range from about 20 to about 50 weight %, in one embodiment in the range from about 25 to about 40 weight %, or in one embodiment in the range from about 33 to about 37 weight %;
       iii. Mo in the range from about 2 to about 20 weight %, in one embodiment in the range from about 5 to about 15 weight %, or in one embodiment in the range from about 9 to about 10.5 weight %;
       iv. Co in the range from about 10 to about 50 weight %, in one embodiment in the range from about 20 to about 40 weight %, or in one embodiment in the range from about 33 to about 37 weight %.
    wherein each weight % is based on the total weight of the mixture prepared for melting;
    b) Melting the mixture in a vacuum induction melting step in order to obtain a first melt, in one aspect of this embodiment, one or more further vacuum induction melting steps are carried out;
    c) Solidifying the first melt in order to obtain a first solid;
    d) Melting the first solid in a vacuum arc melting step in order to obtain a further melt;
    e) Solidifying the further melt in order to obtain a further solid.

12. The process according to embodiment 11, wherein pressure in step b) is below about 0.1 bar, in one embodiment below about 0.05 bar, or in one embodiment below about 0.01 bar.

13. The process according to embodiment 11 or 12, wherein the leak rate in step b) is below about 0.1 bar/min, in one embodiment below about 0.05 bar/min, or in one embodiment below about 0.01 bar/min.

14. The process according to any of the embodiments 11 to 13, wherein the pressure in step d) is below about 0.05 bar, in one embodiment below about 0.01 bar, or in one embodiment below about 0.005 bar.

15. The process according to any of the embodiments 11 to 14, wherein the leak rate in step d) is below about 0.05 bar/min, in one embodiment less than about 0.01 bar/min, or in one embodiment less than about 0.005 bar/min.

16. The process according to any of the embodiments 11 to 15, further comprising a homogenization step carried out at a temperature in the range from about 900 to about 1300° C., in one embodiment in the range from about 1000 to about 1250° C., or in one embodiment in the range from about 1100 to about 1225° C.

17. The process according to any of the embodiments 11 to 16, further comprising a cogging step carried out at a temperature in the range from about 900 to about 1300° C., in one embodiment in the range from about 1000 to about 1250° C., or in one embodiment in the range from about 1100 to about 1225° C.

18. The process according to any of the embodiments 11 to 17, further comprising a finish roll step carried out at a temperature in the range from about 900 to about 1300° C., in one embodiment in the range from about 1000 to about 1250° C., or in one embodiment in the range from about 1100 to about 1225° C.

19. The process according to any of the embodiments 11 to 18, further comprising a straightening step. In one aspect of this embodiment, the straightening is a hot straightening, in one embodiment carried out at a temperature in the range from about 900 to about 1200° C., in one embodiment in the range from about 950 to about 1100° C., or in one embodiment in the range from about 1000 to about 1075° C. In one aspect of this embodiment, the straightening is a cold straightening, in one embodiment carried out at ambient temperature, in one embodiment at a temperature in the range from about 10 to about 100° C., or in one embodiment in the range from about 15 to about 80° C., or in one embodiment in the range from about 20 to about 50° C.

20. An alloy obtainable by a process according to any of the embodiments 11 to 19.

21. An electrical wire comprising an alloy according to any of the embodiments 1 to 10 or 20.

22. A medical device comprising a wire according to embodiment 21.

23. A pacemaker, an implantable cardioverter defibrillator, a cardiac resynchronisation device, a neuromodulation device, a cochlea implant or any other implantable stimulation device comprising a wire according to embodiment 21.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

The embodiments will now be detailed by way of exemplary embodiments with reference to the attached drawings.

DETAILED DESCRIPTION

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the invention. The following detailed description, therefore, is not to be taken in a limiting sense, and the scope of the invention is defined by the appended claims.

It is to be understood that the features of the various exemplary embodiments described herein may be combined with each other, unless specifically noted otherwise.

Although specific embodiments have been illustrated and described herein, it will be appreciated by those of ordinary skill in the art that a variety of alternate and/or equivalent implementations may be substituted for the specific embodiments illustrated and described without departing from the scope of the invention. This application is intended to cover any adaptations or variations of the specific embodiments discussed herein. Therefore, it is intended that this invention be limited only by the claims and the equivalents thereof.

Figure 1:
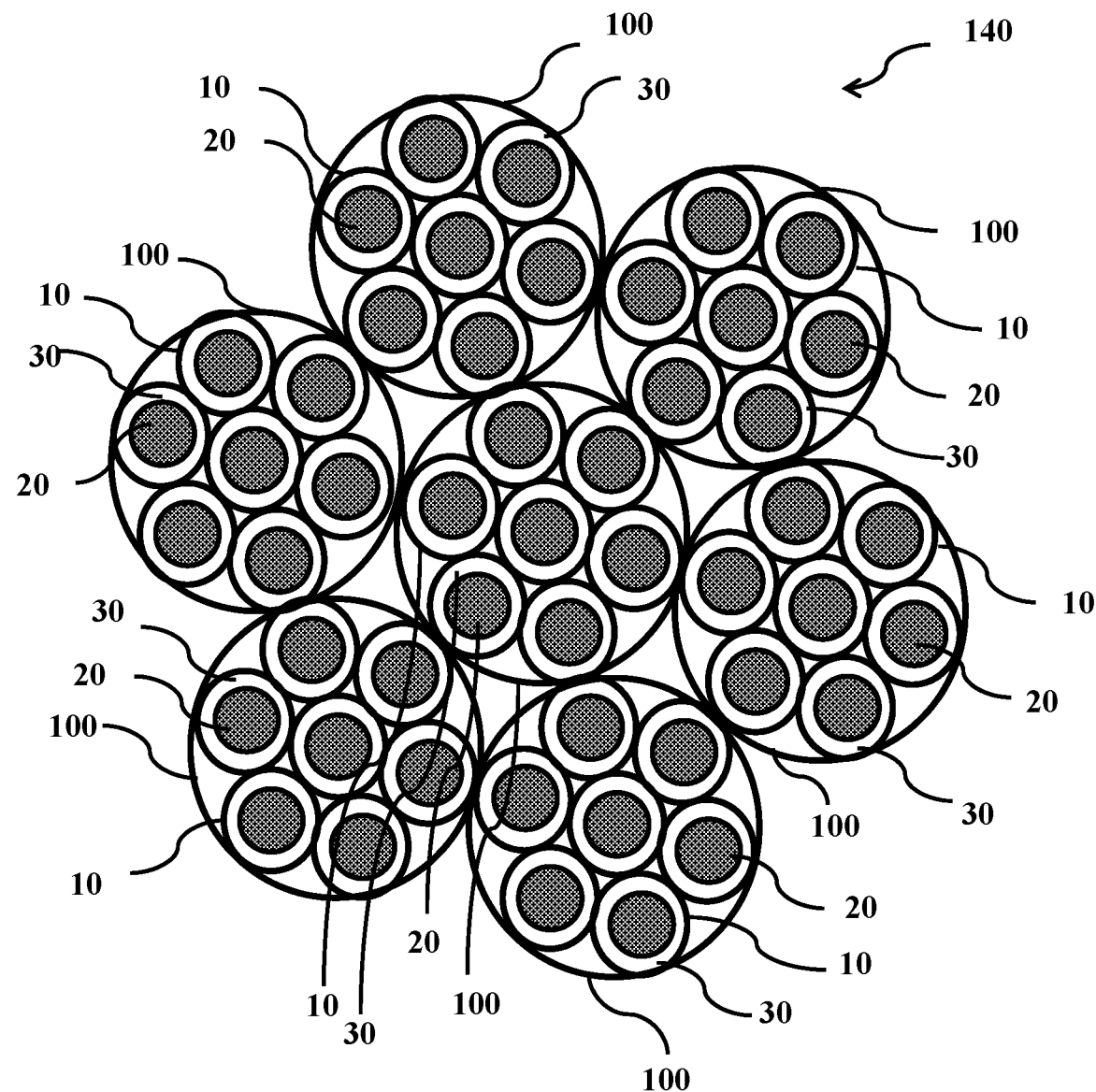
FIG. 1 illustrates schematically a lead according to one embodiment.

FIG. 1 illustrates schematically a lead having a cable bundle 140, which includes cables 100. In this example, the cables 100 each include 7 wires 10. Each wire includes a first region 20 and a further region 30, wherein the first region 20 is interior to the region 30 along the length of the lead 140. The first region 20 is 41 area % of the cross sectional area the wire 10 and the further region is 59 area % of the cross sectional area of the wire 10, in each case based on the total cross sectional area of the wire 10. In this example, the first region 20 is silver. The further region 30 is an alloy according to one embodiment. In this example, the cable bundle 140 includes 7 cables 100, each cable 100 comprising 7 wires 10. The invention is not limited to this arrangement. In one embodiment, other arrangements of wires 10 in cables 100 and/or other arrangements of cable bundles 140 in leads are conceivable.

Figure 2:
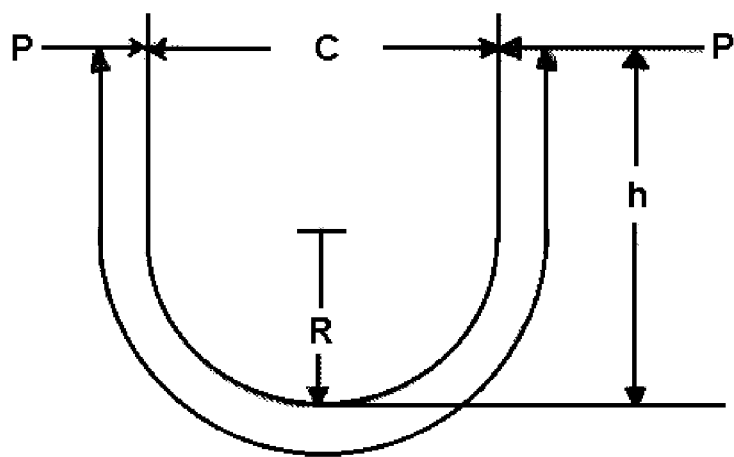
FIG. 2 illustrates schematically an apparatus for measuring fatigue resistance.

FIG. 2 illustrates schematically an apparatus for measuring fatigue resistance.

Figure 3:
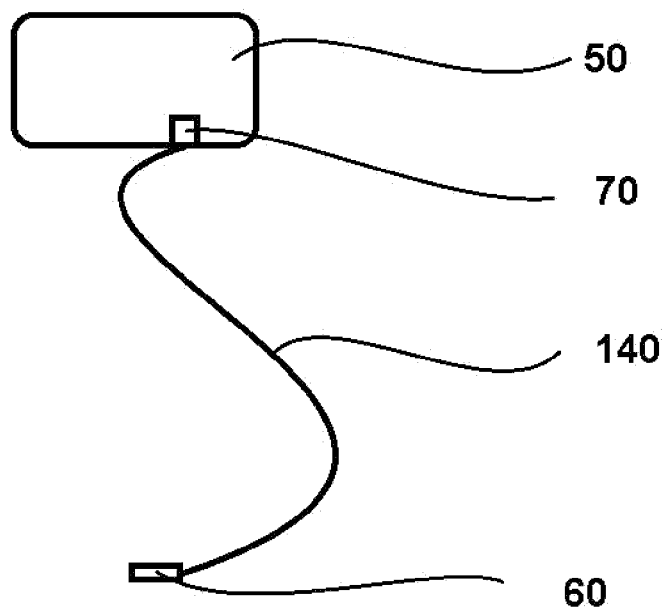
FIG. 3 illustrates schematically a pacemaker comprising a lead according to one embodiment.

FIG. 3 illustrates schematically a pacemaker 50 with a pulse generator 70, and a lead 140 comprising an electrode 60. The lead 140 connects the pulse generator 70 and the heart tissue via the electrode 60.

Figure 4:
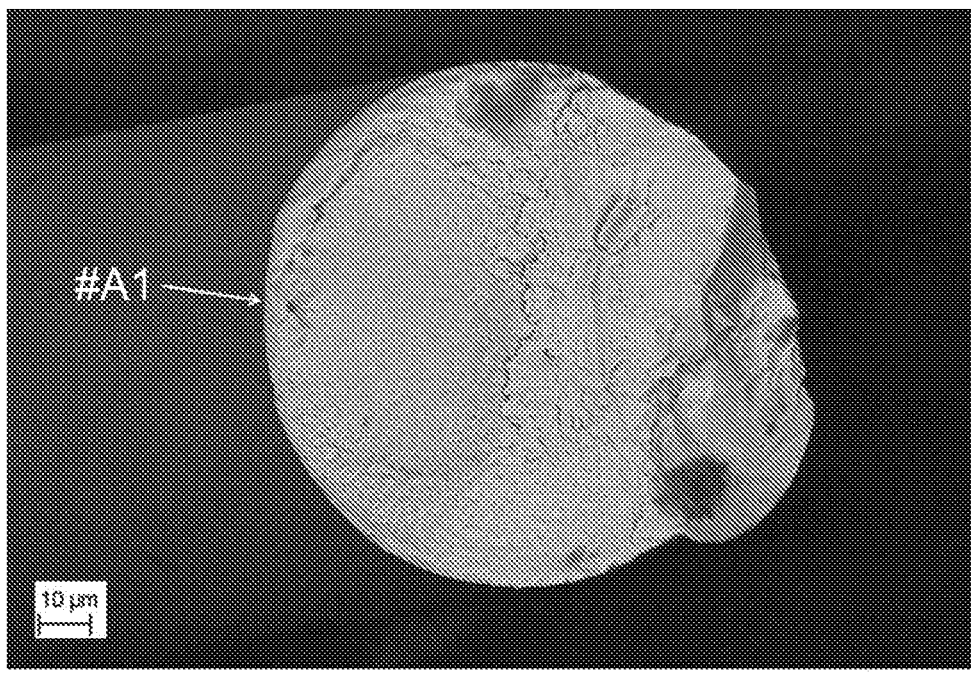
FIG. 4 illustrates a cross sectional image of a wire of material according to example 2 (comparative).

FIG. 4 illustrates a cross sectional image of a wire of material according to example 2 (comparative) as observed by backscattered electron imaging according to the test method. A dark inclusion #A1 is indicated with an arrow.

Figure 5:
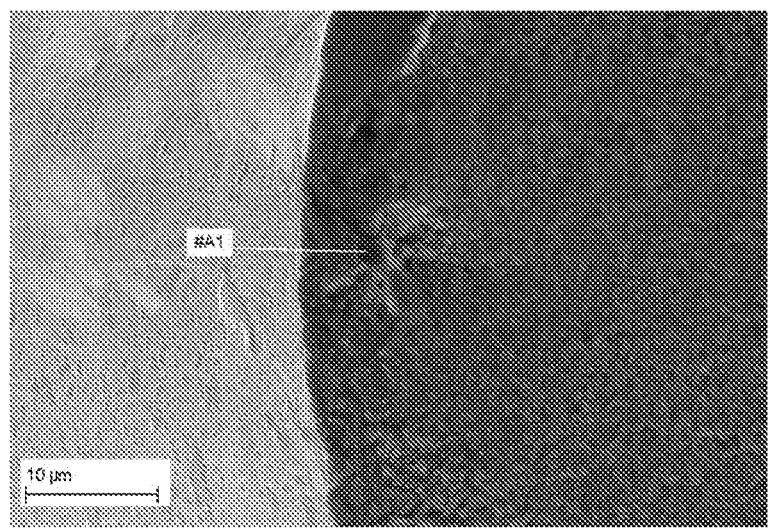
FIG. 5 illustrates a cross sectional image of a wire of material according to example 2 (comparative).

FIG. 5 illustrates a cross sectional image of a wire of material according to example 2 (comparative) as observed by backscattered electron imaging according to the test method. FIG. 5 illustrates the same image as FIG. 4, but at higher magnification. A dark inclusion is indicated with the reference mark #A1.

Figure 6:
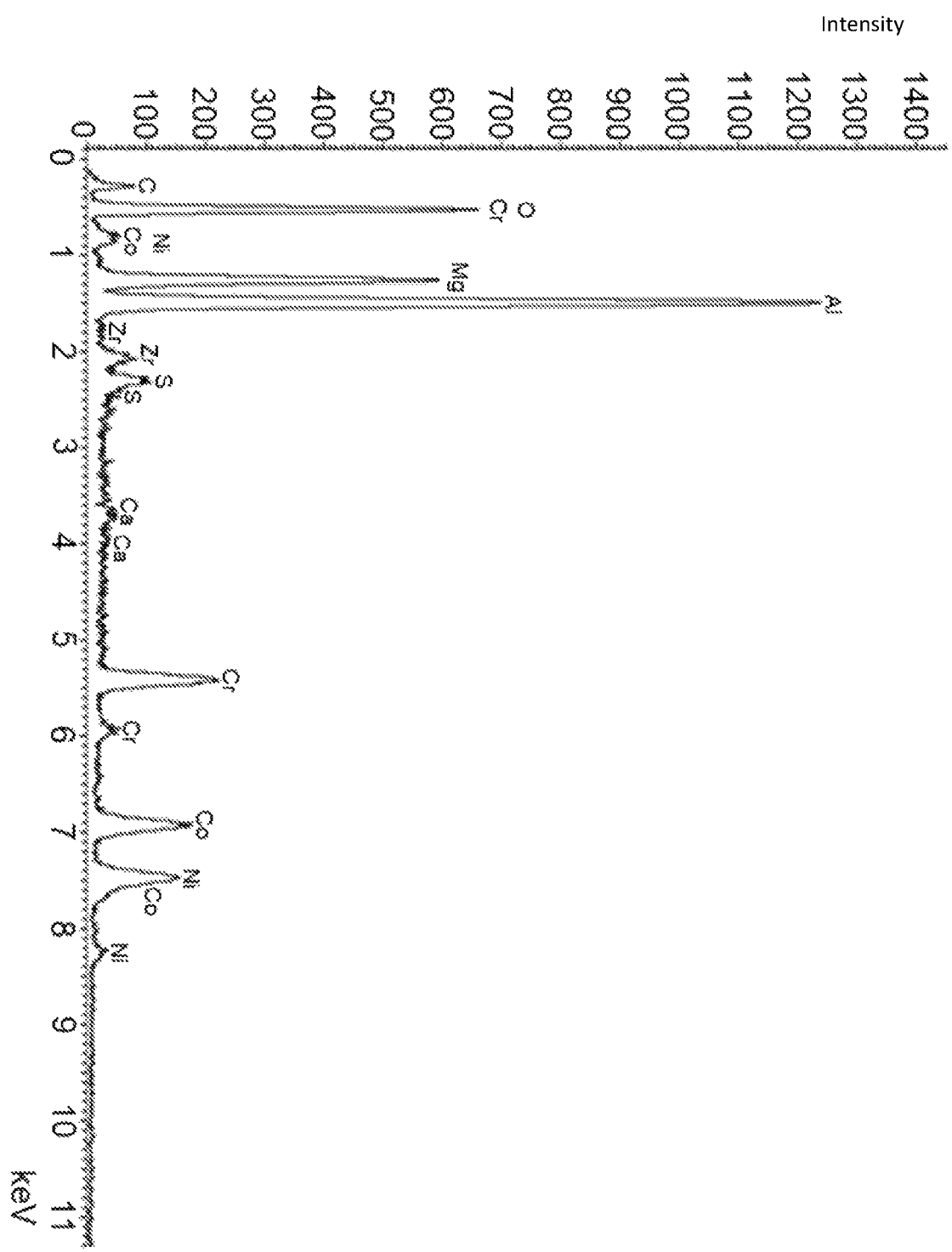
FIG. 6 illustrates an analysis of elemental composition by energy dispersive x-ray spectroscopy of an inclusion in a wire of material according to example 2 (comparative).

FIG. 6 illustrates an analysis of elemental composition by energy dispersive x-ray spectroscopy according to the fracture surface analysis test method of the surface of an inclusion in a wire of material according to example 2 (comparative). The surface analyzed is the inclusion indicated as #A1 in FIG. 5. For example, the analysis illustrates the presence of Al and Mg impurities and also of entities with a Cr—O bond.

Figure 7:
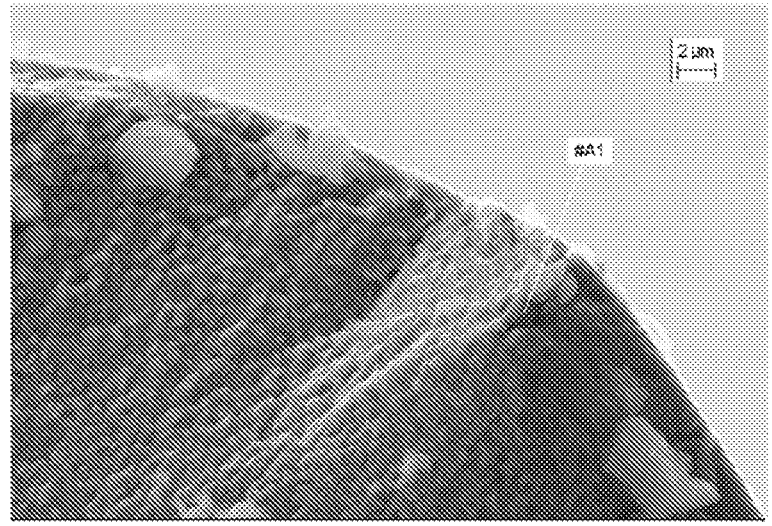
FIG. 7 illustrates a cross sectional image of a wire of material according to example 2 (comparative).

FIG. 7 illustrates a cross sectional image of a wire of material according to example 2 (comparative) as observed by backscattered electron imaging according to the test method. A dark inclusion is indicated with the reference mark #A1.

Figure 8:
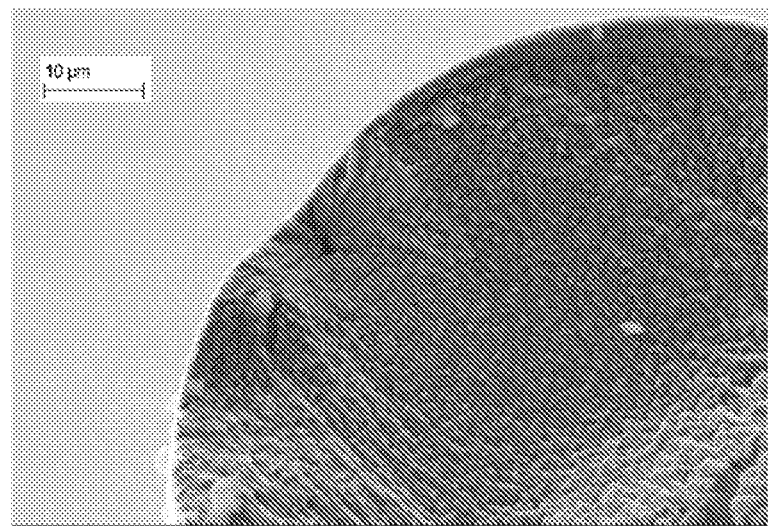
FIG. 8 illustrates a cross sectional image of a wire of material according to example 2 (comparative).

FIG. 8 illustrates a cross sectional image of a wire of material according to example 2 (comparative) as observed by backscattered electron imaging according to the test method. The surface illustrated in FIG. 8 is taken from the same slice as that of FIG. 7.

Figure 9:
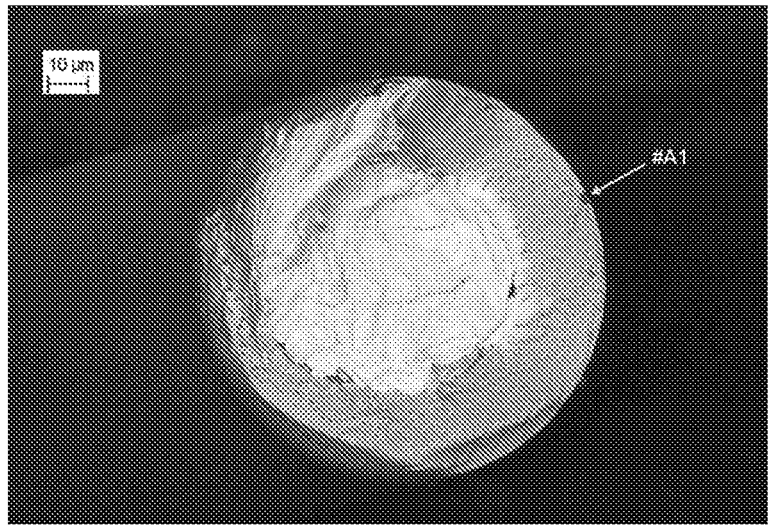
FIG. 9 illustrates a cross sectional image of a wire of material according to example 2a (comparative) with an Ag core.

FIG. 9 illustrates a cross sectional image of a wire of material according to example 2a (comparative) with an Ag core, as observed by backscattered electron imaging according to the test method. A dark inclusion #A1 is indicated with an arrow.

Figure 10:
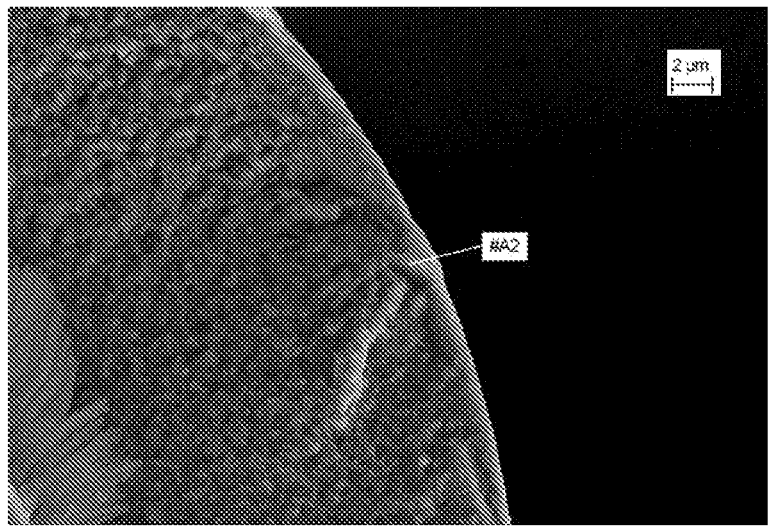
FIG. 10 illustrates a cross sectional image of a wire of material according to example 2a (comparative) with an Ag core.

FIG. 10 illustrates a cross sectional image of a wire of material according to example 2a (comparative) with an Ag core, as observed by backscattered electron imaging according to the test method. FIG. 10 illustrates the same image as FIG. 9, but at higher magnification. A dark inclusion is indicated with the reference mark #A2.

Figure 11:
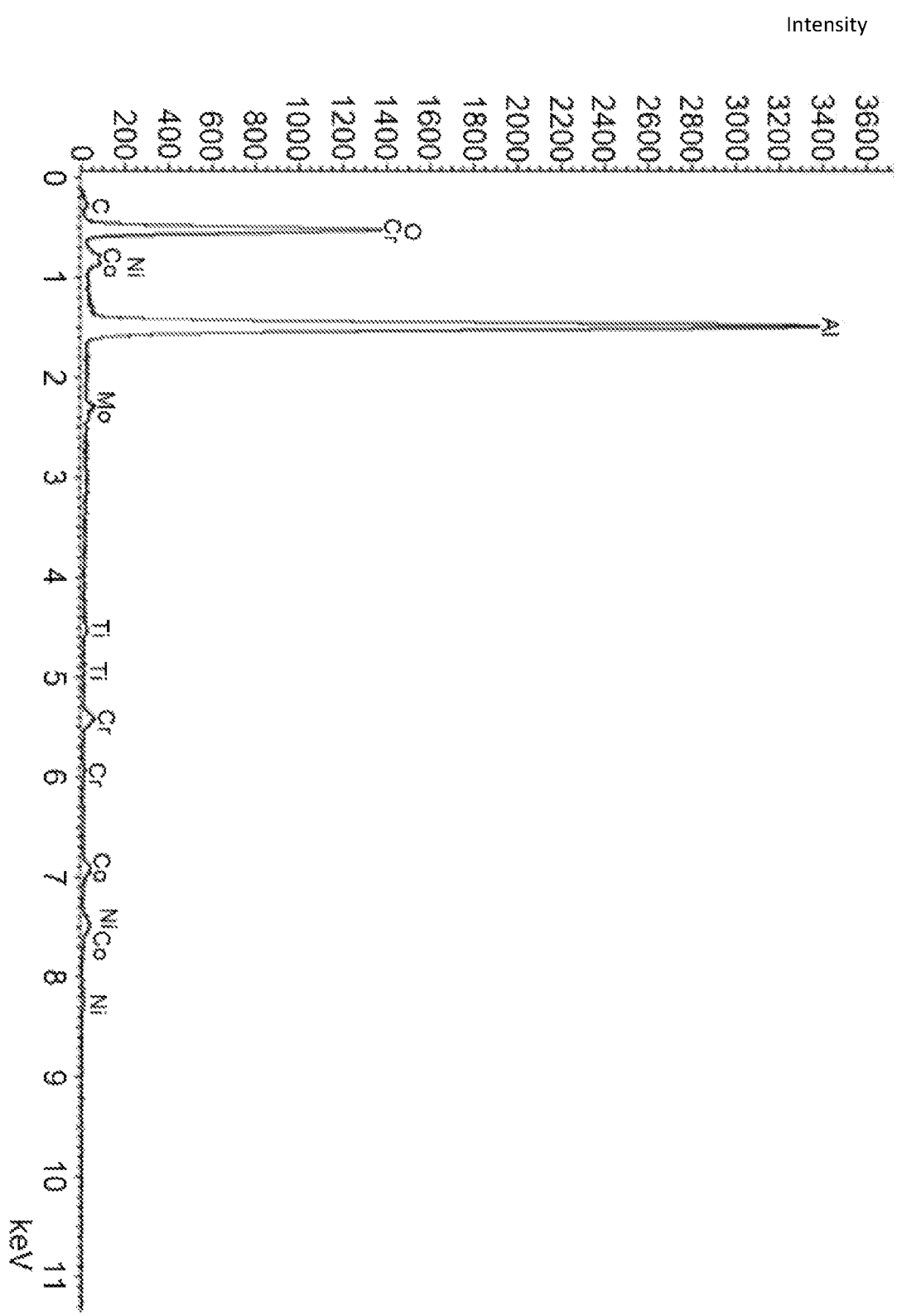
FIG. 11 illustrates an analysis of elemental composition by energy dispersive x-ray spectroscopy of an inclusion in a wire of material according to example 2a (comparative) with an Ag core.

FIG. 11 illustrates an analysis of elemental composition by energy dispersive x-ray spectroscopy according to the fracture surface analysis test method of the surface of an inclusion in a wire of material according to example 2a (comparative) with an Ag core. The surface analyzed is the inclusion indicated as #A2 in FIG. 10. In particular, the analysis illustrates the presence of Al impurities and also of entities with a Cr—O bond.

Figure 12:
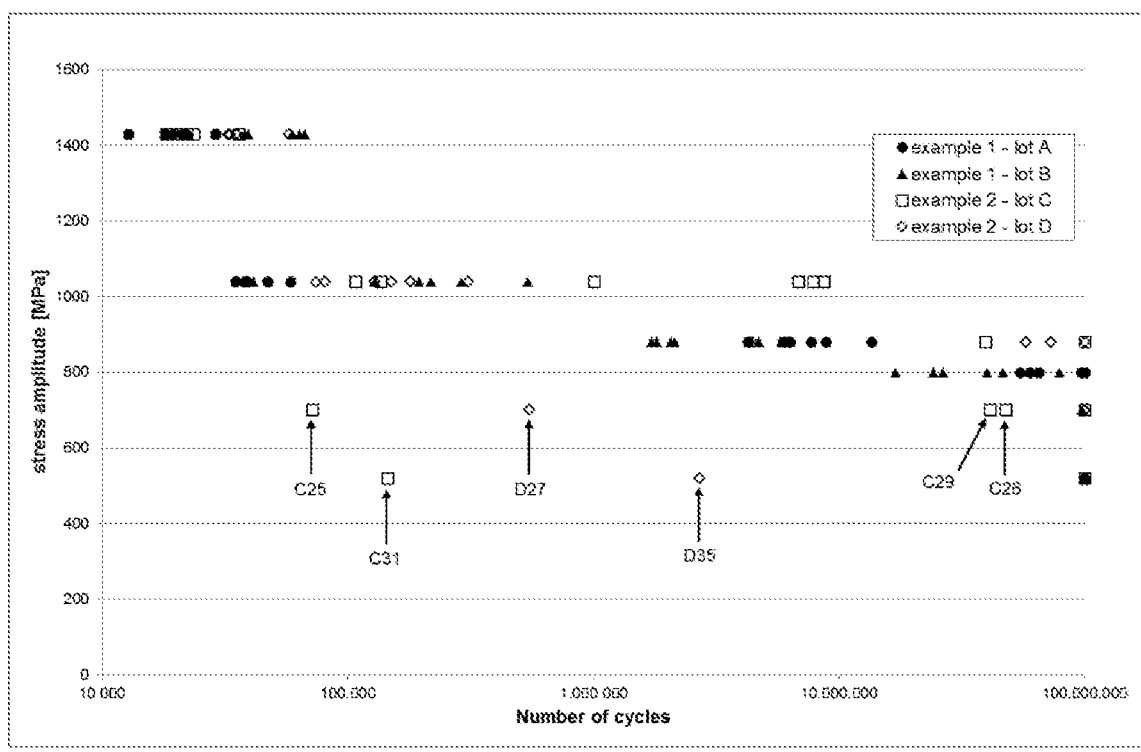
FIG. 12 illustrates a plot of fatigue results for a wire of material according to example 1 (inventive) and a wire of material according to example 2 (comparative).

FIG. 12 illustrates a plot of fatigue results for a wire of material according to example 1 (inventive) and a wire of material according to example 2 (comparative). For example 1 (inventive), results are illustrated for 2 lots, lot A as represented by a solid circle and lot B as represented by a solid triangle. For example 2 (comparative), results are illustrated for 2 lots, lot C as represented by a hollow square and lot D as represented by a hollow diamond. The number of cycles before failure is illustrated as dependent on the stress amplitude applied in the test. Outliers which performed poorly are indicated with arrows.

Figure 13:
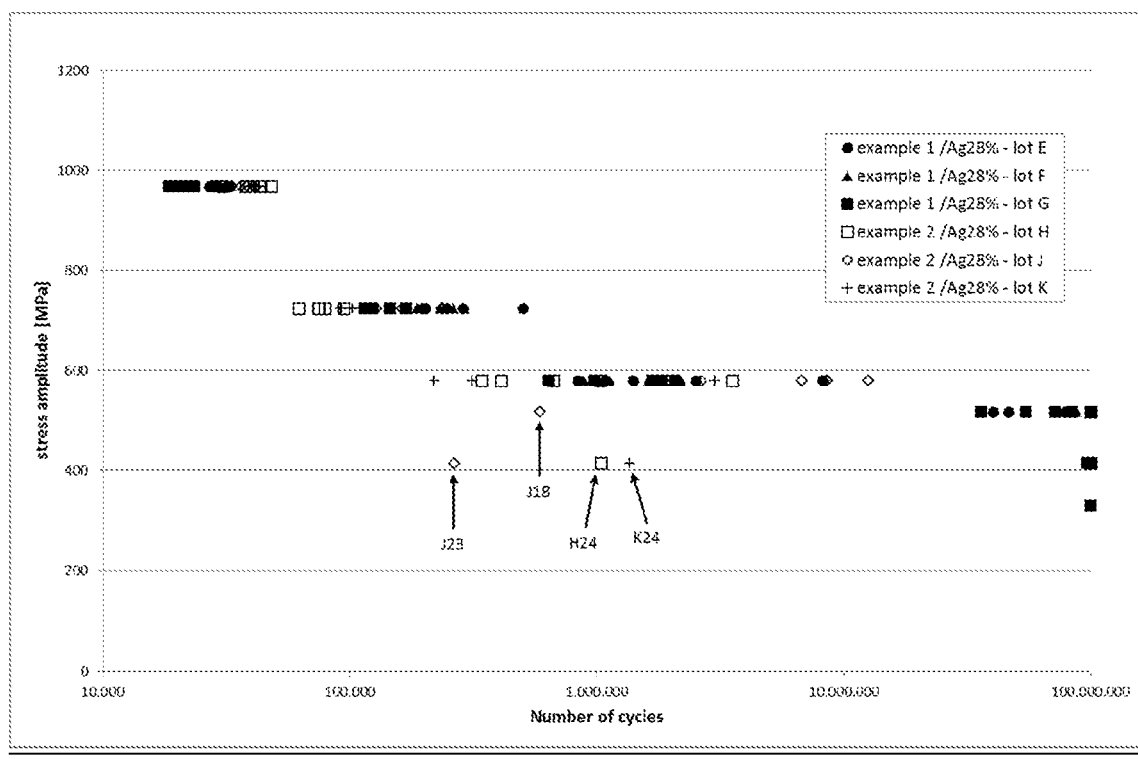
FIG. 13 illustrates a plot of fatigue results for a wire of material according to example 1a (inventive) with an Ag core and a wire of material according to example 2a (comparative) with an Ag core.

FIG. 13 illustrates a plot of fatigue results for a wire of material according to example 1a (inventive) with an Ag core and a wire of material according to example 2a (comparative) with an Ag core. For example 1a (inventive), results are illustrated for 3 lots, lot E as represented by a solid circle, lot F as represented by a solid triangle and lot G as represented by a solid square. For example 2a (comparative), results are illustrated for 3 lots, lot H as represented by a hollow square, lot J as represented by a hollow diamond and lot K as represented by a cross. The number of cycles before failure is illustrated as dependent on the stress amplitude applied in the test. Outliers which performed poorly are indicated with arrows.

Alloy

Preferred alloys according to one embodiment include two or more elements, in one embodiment a solid mixture, with an enthalpy of mixing of the constituent elements of less than about 10 KJ/mol, in one embodiment less than about 5 KJ/mol, and in one embodiment less than about 1 KJ/mol. Preferred alloys include Cr, Ni, Mo and Co as major constituents, in one embodiment with at least about 95 weight %, and in one embodiment at least about 99 weight %, further more in one embodiment at least about 99.9 weight %, and in one embodiment at least about 99.95 weight % of the alloy being Cr, Ni, Mo and Co.

A composition of the alloy is preferred which improves favorable properties of the alloy, for example resistance to fatigue or corrosion resistance, or both.

It is preferred for the properties of the alloy to be improved by limiting the content of impurities or limiting the content of a combination of different impurities, according the disclosed embodiments.

It is preferred that there be a low, or zero concentration of inclusions in the alloy. In one embodiment, this is achieved by limiting the content of impurities. In one embodiment it is preferred that the alloy contain less than about 0.01%, in one embodiment less than about 0.005%, or in one embodiment less than about 0.001% inclusions. The % of inclusions is in one embodiment determined using the microscopic inspection method given in the test methods. Content of inclusions as % is there determined as the proportion of the cross sectional area of the sample surface made up of inclusions. In some instances, the alloy includes a low, or in one embodiment a zero concentration of inorganic non-metallic solid inclusions, more in one embodiment of inorganic oxide inclusions. Inorganic oxides in this context can refer to metal oxides, non-metal oxides and metalloid-oxides. In some cases the alloy includes a low, or in one embodiment a zero concentration of inclusions comprising one or more selected from the group consisting of: Si, Al, Ti, Zr and B; in one embodiment selected form the group consisting of: Si Ti, and Al.

In one embodiment, one or more treating material(s) is/are contacted with the mixture of the process in order to remove oxygen from the mixture of the process, in one embodiment by incorporation of the oxygen into a dross and removal of the dross. Preferred treating materials in this context include one or more selected from the list consisting of: Al, Mg, Ca and Ce; in one embodiment in the form of an element and/or in the form of an alloy, wherein the alloy in one embodiment contains a further metal being selected from group consisting of Cr, Ni, Mo and Co or at least two thereof, in one embodiment Ni.

In order to achieve the preferred concentrations of constituents of the alloy, described above in the embodiments, the skilled person may vary the proportions of starting materials employed in the preparation process. The proportions of the starting materials might not be equal to the proportions of constituents of the product, due to net loss or gain during the preparation process.

Process for Preparation of the Alloy

The process for the preparation of the alloy in one embodiment includes the following steps:
  a) A vacuum induction melting step;
  b) A vacuum arc melting step.

In one embodiment, the process includes two or more vacuum induction melting steps. In another embodiment, the process includes two or more vacuum melting steps. In another embodiment, the process includes two or more vacuum induction melting steps and two or more vacuum arc melting steps.

In preferred embodiments, the process further includes one or more of the following steps:
  c) An electro-slag melting step
  d) A homogenization step
  e) A cogging step
  f) A finish roll step
  g) A straightening step In preferred embodiments, the process includes a combination of the above steps selected from the list consisting of: c), d), e), f), g), c)+d), c)+e), c)+f), c)+g), d)+e), d)+f), d)+g), e)+f), e)+g), f)+g), c)+d)+e), c)+d)+f), c)+d)+g), c)+e)+f), c)+e)+g), c)+f)+g), d)+e)+f), d)+e)+g), d)+f)+g), e)+f)+g), d)+e)+f)+g), c)+e)+f)+g), c)+d)+f)+g), c)+d)+e)+g), c)+d)+e)+f) and c)+d)+e)+f)+g).

In one embodiment, one or more of the steps c)-g) is carried out two or more times.

In preferred vacuum induction melting steps, a material is heated by inducing an electric current in the material, in one embodiment by electromagnetic induction. The pressure in the vacuum induction melting step is in one embodiment below about 0.1 mbar, or in one embodiment below about 0.01 mbar, or in one embodiment below about 0.001 mbar. The vacuum induction melt step is in one embodiment carried out in an oven, in one embodiment with a low leak rate, in one embodiment below about 0.1 mbar·l/s, or in one embodiment below about 0.01 mbar·l/s, or in one embodiment below about 0.001 mbar·l/s. The leak rate is in one embodiment tested before the vacuum induction melting step by evacuating the oven, closing the valves of the oven, and measuring the rate of increase of pressure in the oven.

In one embodiment, the vacuum induction melting step is carried out in an inert atmosphere, in one embodiment argon, in one embodiment an atmosphere comprising at least about 90 weight %, or in one embodiment at least about 99 weight %, or in one embodiment at least about 99.9 weight % of inert gas, in one embodiment argon. In one aspect of this embodiment, the oven is evacuated and inert gas, in one embodiment argon, introduced into the oven before melting. In one aspect of this embodiment, the pressure in the vacuum induction melting step is in the range from about 1 to about 200 mbar, in one embodiment in the range from about 10 to about 150 mbar, or in one embodiment in the range from about 20 to about 100 mbar.

In preferred vacuum arc melting steps, a material is heated by passing an electrical current through the material, in one embodiment with an electrical power in the range from about 300 to about 1200 W/kg, or in one embodiment in the range from about 400 to about 1000 W/kg, or in one embodiment in the range from about 450 to about 900 W/kg, based on the mass of material heated. The pressure in the vacuum arc melting step is in one embodiment below about 0.1 mbar, or in one embodiment below about 0.01 mbar, or in one embodiment below about 0.001 mbar. The vacuum arc melt step is in one embodiment carried out in an oven, in one embodiment with a low leak rate, in one embodiment below about 0.1 mbar·l/s, or in one embodiment below about 0.05 mbarl/s, or in one embodiment below about 0.01 mbar·l/s. The leak rate is in one embodiment tested before the vacuum arc melting step by evacuating the oven, closing the valves of the oven, and measuring the rate of increase of pressure in the oven. In one embodiment, the vacuum arc melting step is carried out in an inert atmosphere, in one embodiment argon, in one embodiment an atmosphere comprising at least about 90 weight %, or in one embodiment at least about 99 weight %, or in one embodiment at least about 99.9 weight % of inert gas, in one embodiment argon.

In one aspect of this embodiment, the oven is evacuated and inert gas, in one embodiment argon, introduced into the oven before melting. In one aspect of this embodiment, the pressure in the vacuum arc melting step is in the range from about 0.001 to about 0.2 bar, in one embodiment in the range from about 0.01 to about 0.15 bar, or in one embodiment in the range from about 0.05 to about 0.1 bar.

Homogenization steps according to one embodiment allow reduction of inhomogeneity in a material, in one embodiment by heating. In preferred homogenization steps according to one embodiment, a material is heated to a temperature which is below its melting temperature, in one embodiment below its incipient melting temperature. It is preferred that the material be homogenized for a duration in the range from about 10 min. to about 20 hours, or in one embodiment in the range from about 3 hours to about 10 hours, or in one embodiment in the range from about 5 hours to about 8 hours. Homogenization is in one embodiment carried out in a vacuum or in a gaseous atmosphere, in one embodiment in a gaseous atmosphere. It is preferred that the homogenization step be carried out close to atmospheric pressure, in one embodiment in the range from about 0.5 to about 1.5 bar, or in one embodiment in the range from about 0.8 to about 1.2 bar, or in one embodiment in the range from about 0.9 to about 1.1 bar. In one preferred embodiment, the homogenization step is carried out in air.

In preferred cogging steps according to one embodiment, the porosity or grain size or both of a material are reduced, in one embodiment at elevated temperatures, in one embodiment below the melting point of the material, in one embodiment with the application of compressive force. Compressive forces may be applied locally or in a delocalized manner, in one embodiment by one or more selected from the group consisting of: rolling, pressing, beating and turning. Where the material to be cogged has a mass below about 10 kg, in one embodiment below about 8 kg, or in one embodiment below about 5 kg, rolling is preferred. Where the material to be cogged has a mass above about 10 kg, in one embodiment above about 20 kg, or in one embodiment above about 30 kg, beating or turning is preferred. It is preferred that the smallest dimension of the material is reduced during the cogging process.

Preferred finish roll steps according to one embodiment reduce the smallest dimension of the material, in one embodiment by passing the material through one or more pairs of rolls, in one embodiment below the melting point of the material, or in one embodiment below its incipient melting point. In one embodiment, the finish roll step reduces the porosity or grain size of the material, or in one embodiment both.

Straightening in one embodiment reduces the physical curvature of the material, in one embodiment so as to facilitate further grinding or machining steps. Straightening is in one embodiment carried out by applying compressive force. The straightening step is in one embodiment carried out below the melting point of the material, or in one embodiment below its incipient melting point. In one embodiment, the process includes a hot straightening step. In one embodiment, the process includes a cold straightening step, in one embodiment carried out at around ambient temperature. Cold straightening is in one embodiment carried out at a temperature in the range from about 10 to about 100° C., or in one embodiment in the range from about 15 to about 80° C., or in one embodiment in the range from about 20 to about 50° C.

Leads, Wires and Medical Devices

In this text, reference is made variously to a coated or cladded wire, which includes a wire core and a shell. The shell might be coated or cladded onto the core wire.

A preferred lead according to one embodiment includes at least one proximal connector, at least one distal electrode and a flexible elongated conductor that is electrically connecting the electrode(s) to the connector(s). Preferably the elongated conductor is a coiled wire or a cable and includes the alloy according to one embodiment.

A contribution to achieving at least one of the above mentioned objects is made by a wire including an alloy according to one embodiment, having a thickness in the range from about 10 to about 50 µm, in one embodiment in the range from about 15 to about 35 µm. In one embodiment, the wire further includes silver metal.

In one embodiment, the lead includes a silver core and an alloy according to one embodiment, present as a shell surrounding the silver core.

A contribution to achieving at least one of the above mentioned objects is made by a lead comprising one or more wires according to one embodiment, grouped into two or more cables, each cable comprising two or more wires according to one embodiment. In one embodiment, the cables have a thickness in the range from about 0.05 to about 0.5 mm, in one embodiment in the range from about 0.1 to 0.4 mm.

A contribution to achieving at least one of the above mentioned problems is made by a medical device, in one embodiment a pacemaker, comprising a lead according to one embodiment. A preferred pacemaker in one embodiment includes:

An implantable pulse generator;
One or more leads according to one embodiment.

In one embodiment, the pacemaker includes one or more pulsers.

In one embodiment, the pacemaker includes one or more energy cells, in one embodiment one or more electrical cells.

A preferred process for the preparation of a wire according to one embodiment includes the steps:

a) Providing a tube of alloy according to one embodiment;
b) At least partially filling the tube with Ag to obtain a composite;
c) One or more drawing steps to reduce the diameter of the composite;
d) Optionally one or more annealing steps to soften the composite and facilitate drawing.

In one embodiment, the Ag content of the wire obtainable by the process is in the range from about 15 to about 50 weight %, in one embodiment in the range from about 17.5 to about 45.7 weight %, or in one embodiment in the range from about 28.7 to about 37.7 weight %, based on the total weight of the wire.

In one embodiment the diameter of the wire obtainable by the process is in the range from about 5 to about 50 µm, in one embodiment in the range from about 15 to about 35 µm.

In one embodiment, the filling degree of silver in the wire obtainable by the process is in the range from about 15% to about 41%, in one embodiment in the range from about 20% to about 35%, or in one embodiment in the range from about 23% to about 33%.

Test Methods

Alloy Composition

For a quantitative chemical analysis of the alloy, the following methods are used:

a) the main components of the alloy (Co, Cr, Ni, Mo) are measured by X-ray fluorescence XRF using the XRF Lab Report—S8 TIGER from the company BRUKER (Bruker AXS GmbH Östliche Rheinbrückenstr. 49, 76187 Karlsruhe, Germany)

b) Trace elements present in the alloy (Mn, P, Si, Fe, Ti, Al, B, Mg, Ca, Ce, Ti) are measured by glow discharge mass spectrometry (GDMS) using the ASTRUM from Nu Instruments (Nu Instruments Limited, Unit 74, Clywedog Road South, Wrexham, LL13 9XS UK.)

c) Gas or non-metallic components in the alloy (H, O, C, N, S) are measured by carrier-gas hot extraction using the ONH836 from LECO (LECO Corporation, 3000 Lakeview Avenue, St. Joseph, Mich. 49085)

Leak Rate

The leak rate of the furnace chamber is measured using the following procedure:

The Vacuum furnace chamber is evacuated to the required pressure by a vacuum pumping station. When the required pressure is reached, the pressure valve between the vacuum furnace chamber and the vacuum pumping station is closed. The pressure increase of the vacuum furnace chamber over a given length of time defines the leak rate of the equipment.

Fatigue Resistance

Rotating beam fatigue testing was carried out using Valley Instruments model #100 test machine (FIG. 2) according to Valley Instruments Wire Fatigue Tester Model #100 user manual (Valley Instruments, Division of Positool Technologies, Inc., Brunswick, Ohio, USA. Fatigue Tester Model 100 Manual). The equipment consists of a synchronous motor rotating at 3600 rpm. For each test of a wire specimen, a sample having a predefined length is fixed in a custom fine-wire collet at one end, looped through a complete 180 degree turn and is placed at the other end in a low-friction bushing in which it is free to rotate. The synchronous motor of the test device is directly clocked by a counter where the number of cycles is illustrated in a LCD-display. The fatigue testers are equipped with a sensor to detect the wire fracture which automatically stops the timer, which means the display of the timer illustrates the number of cycles until failure. If no fracture occurs within 100 Million cycles, the test is stopped.

Valley Instruments Wire Fatigue Tester Model #100 user manual (Valley Instruments, Division of Positool Technologies, Inc., Brunswick, Ohio, USA. Fatigue Tester Model 100 Manual) describes that a loop, formed by an elastic length held so that the axes of the specimen at the point of retention are exactly parallel, assumes a shape in which:
(1) The length of the loop is 2.19 times the base,
(2) The height of the arch is always 0.835 times the base,
(3) The minimum radius of the curvature occurs at the apex of the arch and is exactly 0.417 times the base, and
(4) The bending stress at the point of minimum curvature bears a simple reciprocal linear relationship to any of the four physical dimensions (length, height, base, and minimum curvature).

The following formulas express the exact relationship:

$$C=1.198*E*d/S$$

$$h=0.835*C$$

$$L=2.19*C$$

$$R=0.417*C$$

$$P=0.141*E*d4/C2$$

Nomenclature:
C=chuck to bushing distance
d=diameter of wire
h=height of loop
E=modulus of elasticity
L=length of wire external to chucks
R=minimum of radius of curvature
S=bending stress
P=bushing load or lateral force at the chuck With the above listed formula, the bending stress S (at the peak of the loop) can be calculated by the following equation:

$$S=1.198*E*d/C$$

The machine set-up involves calculating the desired sample length and center distance using the modulus of elasticity of the material and equations developed by Valley Instruments Company (user manual).

Microscopic Inspection Method for Micro-Cleanliness

Definition

Inclusions are defined as internal flaws or contaminations (such as nitrides or oxides) within the billet or rod from which the wire or tube is produced. The transverse inclusion size is defined as the largest dimension of an internal flaw measured on transverse cross-sections of the billet, rod or wire. The longitudinal inclusion size is defined as the largest dimension of an internal flaw measured on longitudinal cross-sections of the billet, rod or wire. A cross-section diametric line is defined as any line within the cross-section having a length equal to or greater than 95% of the true cross-section diameter.

General Test Procedure:
a) Sectioning

For each material lot, the billet, rod or wire is to be sectioned at each end so that there are an equal number of cross sections sampled at the one end as there are samples at the other end (number of samples taken from each end shall differ by no more than one). The total number of cross sections samples depends on the diameter of the billet, rod or wire and is specified in Table 1. The length of each cross section is to be less than its diameter.

b) Imaging

For each billet, rod or solid wire cross section, non-overlapping images are to be taken at 500× magnification along diametric lines so that the total examined area per sample is at least 1.77 mm2. A cross section diametric line is defined as any line within the cross section having a length equal to or greater than 95% of the true cross section diameter. Angular separation between two diametric lines on a cross section shall be a minimum of 60 degrees. The number of images and the number of diametric lines depends on the diameter of the billet, rod or wire and is specified in Table 1.

The total number of images is illustrated in Table 1 and was calculated based on the number of images per sample and the number of samples.

c) Measurement

Each of the images is to be inspected to detect the presence of inclusions or strings of inclusions that exceed a size of 3.0 μm in their largest dimension. The image inspection may be accomplished either by manual examination or by automated scanning.

TABLE 1

| cross section diameter of billet, rod or wire | | Number of diametric lines per section (no requirement for tube samples) | Number of images per section | Number of cross-sections | | Total images per lot | |
|---|---|---|---|---|---|---|---|
| equal to or greater than [mm] | but no greater than [mm] | | | transverse | longitudinal | transverse | longitudinal |
| 2.54 | 3.80 | 5 | 40 | 12 | 12 | 480 | 480 |
| 3.81 | 5.71 | 3 | 40 | 12 | 12 | 480 | 480 |
| 5.72 | 11.42 | 2 | 40 | 12 | 12 | 480 | 480 |
| 11.43 | 13.96 | 1 | 40 | 12 | 12 | 480 | 480 |
| 13.97 | 17.14 | 1 | 48 | 10 | 10 | 480 | 480 |
| 17.15 | 21.58 | 1 | 60 | 8 | 8 | 480 | 480 |
| 21.59 | 27.93 | 1 | 80 | 6 | 6 | 480 | 480 |
| 27.94 | 33.01 | 1 | 96 | 5 | 5 | 480 | 480 |
| 33.02 | 43.17 | 1 | 120 | 4 | 4 | 480 | 480 |
| 43.18 | 57.14 | 1 | 160 | 3 | 3 | 480 | 480 |

Fracture Surface Analysis of Wire Samples

The test method to analyze fracture surfaces of fatigue tested samples was Scanning electron microscopy (SEM). A Zeiss Ultra 55 Gemini was used for the sample analysis of one embodiment and comparative samples.

Two imaging modes were used to analyze and illustrate the tested samples.
a) SE: the detection of secondary electrons (SE) results in images with a well-defined, three-dimensional appearance. The surface topography can be illustrated in high resolution. FIGS. 5, 7, 8 and 10 are secondary electron images.
b) BSE: backscatter electrons (BSE) are used to detect contrast between areas with different chemical compositions. Heavy elements (high atomic number) backscatter electrons more strongly than light elements (low atomic number), and thus appear brighter in the image. FIGS. 4 and 9 are BSE images.

Energy-dispersive X-ray spectroscopy (EDS, EDX) was used for the elemental analysis of features (inclusions/particles) found on the fatigue resistance test samples. A high-energy beam of electrons is focused onto the location of the sample being analyzed. This leads to the emission of characteristic X-rays which allows the elemental composition of the feature (inclusions/particles) to be measured. FIGS. 6 and 11 illustrate EDX scans.

EXAMPLES

The MP35N heats were VIM-VAR melted, to minimize the impurity content and to obtain a sound ingot with good chemical uniformity and metallurgical properties. The chemistry of representative heats: Heat 1, Heat 2 and Heat 3 are listed in Table 3. The table also provides the chemistry of a VIM-VAR melted, commercially available MP35N alloy and for reference the chemical requirements per ASTM F562-13, a standard specification for wrought MP35N alloy. The major constituents of MP35N alloy are Co, Ni, Cr and Mo. The new alloy heats were melted in 2 steps. The first melting step was Vacuum Induction Melting (VIM). The VIM furnace consists of a water cooled vacuum melt chamber, an oxide ceramic crucible held in a cylindrical induction heating coil inside the melt chamber, an AC electric power supply, a vacuum pumping system, a raw material adding chamber and a cylindrical metal mold held below and offset from the crucible-induction coil assembly. The vacuum melt chamber, raw material adding chamber and vacuum pumping system are separated by isolation valves. The induction heating coil is water cooled. Electric current from the power supply passes through the induction heating coil creating a magnetic field inside the furnace. The magnetic field induces eddy currents inside the raw materials causing Joule heating. Joule heating raises the temperature of the raw materials to above their melting point. The magnetic field mixes the liquid raw materials to make a homogeneous alloy. The crucible is tilted to pour the liquid alloy from the crucible into the mold. The alloy cools to a solid in the mold under vacuum and is removed from the furnace. The alloy ingot is removed from the mold and it is prepared for re-melting.

For the example heats, 136 kilograms of elemental raw materials were placed in the furnace in proportions calculated to make the aim chemistry. The VIM furnace was closed and pumped down to ≤0.00001 bar. A leak-up rate was measured after reaching the desired vacuum pressure level to ensure a vacuum tight furnace. The leak-up rate was ≤0.00001 bar/min. Electric power was applied to the induction heating coil. Once the melt was in progress, the vacuum level was recorded at specified intervals to monitor the progress of melting and the mixing and reaction of all of the raw materials. When the reactions ceased as indicated by a constant vacuum pressure level, the heat was poured into a 152.4 mm diameter cylindrical mold.

Each heat was subsequently re-melted by a Vacuum Arc Re-melting (VAR) process to make a 203.2 mm diameter ingot. The VAR furnace consists of water cooled vacuum chamber, a 203.2 mm diameter water cooled copper crucible, a direct current electric power supply, a vacuum pumping system, isolation valves and a computer based electrical system to monitor and control the application of current to the electrode inside the vacuum chamber. The furnace was pumped down to ≤0.000006 bar before carrying out the leak-up rate test. A leak rate of ≤0.000006 bar/min was obtained. The electrode was moved to a close proximity to the bottom of the crucible. Electric power was applied at a level to cause an electric arc to be struck between the crucible bottom and the alloy electrode. The electric arc causes the electrode to melt and drip into the bottom of the crucible creating a liquid metal pool that solidifies as the arc moves away from the molten pool. The process was continued at a controlled rate until the electrode was consumed. The power was turned off and the ingot was cooled under vacuum. The ingot was removed from the furnace for processing to product.

The as-cast ingot was charged into a gas-fired front opening box furnace with ambient air atmosphere. The furnace was preset to a temperature of 815° C. Upon equilibration of furnace temperature, the ingot was held for additional 4 hours prior to raising the furnace temperature. The ingot was then heated to 1177° C. at a heating rate of 200 K per hour. The ingot was held for 7 hours at 1177° C. for homogenization. After homogenization, the ingot was hot rolled from 203 mm to 137 mm round cornered square (RCS) billet using a 559 mm diameter Morgenshammer Mill operating at ambient temperature. The Morgenshammer Mill is a manually operated tilt table mill with 3 high rolls allowing heavy bar to be rolled alternately between the bottom and middle roll and the top and middle roll. After hot rolling the RCS billet was air cooled, abrasively ground by hand to remove surface imperfections and cut to square the ends. The billet was reheated and hot rolled to 51 mm RCS at 1177° C. on the 559 mm Morgenshammer Mill. The RCS was cut to shorter lengths of final rolling on a hand operated 406 mm diameter Morgenshammer Mill with 3 high rolls. All bar manipulation on this mill is done by hand at floor level. The RCS was reheated at 1177° C. and rolled to 33.4 mm round bars and air cooled to ambient temperature. The rolled bars were then reheated to 1038° C. and held for 30 minutes for hot rotary straightening. After straightening, the bars were air cooled to room temperature. The bars were rough centerless ground, ultrasonic tested for voids and then centerless ground to final size.

For manufacturing of clad-wires, the grinded bars were gun-drilled to produce hollows for subsequent tube drawing. Tubes were filled with Ag-rods and cold-drawn using diamond dies and mineral oil. For a final wire diameter of 127 µm, the last intermediate annealing was carried out at a wire diameter of 157.5 µm at 900-950° C. in Argon atmosphere. From the last intermediate annealing until the final diameter of the wire, 35% cold-work were applied. Three wire lots were manufactured having UTS values of 1456, 1469 and 1474 MPa. For bare wire, the bars were further hot-rolled to 0.2 inch outer diameter followed by cold-drawing. For 102 µm final size wire, the last intermediate annealing was carried out at a wire diameter of 122 µm at 1100° C. in Argon atmosphere to apply 30% cold-work to the final size. Two wire lots were manufactured having UTS values of 1870 and 1875 MPa. The wires of inventive example 1 (Lots A & B) and the cladded wires of inventive example 1a (Lots E, F & G) were made using the alloy of Heat 1 in table 3. The wires of comparative example 2 (lots C & D) and the cladded wires of comparative example 2a (lots H, J & K) were made from the alloy of the commercial heat in table 3 obtained from Fort Wayne Metals, Inc., USA under the trade name 35 NLT®.

TABLE 2

| Material | Example 1 (inventive) | | Example 1a with 28% Ag (inventive) | | |
|---|---|---|---|---|---|
| Batch | Lot A | Lot B | Lot E | Lot F | Lot G |
| UTS [MPa] | 1870 | 1875 | 1456 | 1469 | 1474 |
| YM [GPa] | 190 | 191 | 121 | 121 | 122 |
| Elongation [%] | 2.8 | 2.9 | 2.2 | 2.3 | 2.3 |

The processed alloy was also obtainable from SAES Smart Materials, Inc. Alloys for the further examples were acquired from SAES Smart Materials, Inc.

TABLE 3

| Element | Heat 1 Weight % | Heat 2 Weight % | Heat 3 Weight % | Commercial Heat Weight % | ASTM F-562-13 Weight % |
|---|---|---|---|---|---|
| C | 0.0039 | 0.0091 | 0.0106 | 0.005 | <0.0250 |
| B | 0.000065 | 0.000067 | 0.000008 | 0.01 | <0.015 |
| P | 0.00018 | 0.000095 | 0.000056 | 0.001 | <0.015 |
| S | 0.00056 | 0.00026 | 0.00036 | 0.001 | <0.010 |
| Mn | 0.00028 | 0.00021 | 0.00013 | 0.017 | <0.15 |
| Si | 0.0042 | 0.0053 | 0.0061 | 0.034 | <0.15 |
| Al | 0.00023 | 0.00054 | 0.00043 | 0.023 | NA |
| Mg | <0.000001 | 0.000003 | 0.000005 | 0.001 | NA |
| Ca | <0.000005 | <0.000005 | <0.000005 | NA | NA |
| Ce | <0.000001 | <0.000001 | <0.000001 | NA | NA |
| Fe | 0.021 | 0.023 | 0.023 | 0.08 | <1 |
| Ti | 0.00017 | 0.000038 | 0.000023 | 0.001 | <1 |
| O | 0.0085 | 0.0056 | 0.0035 | 0.0021 | NA |
| N | 0.0022 | 0.0009 | 0.0007 | 0.0022 | NA |
| Cr | 19.6 | 19.7 | 20 | 20.62 | 19-21 |
| Ni | 35.7 | 34.8 | 34.9 | 34.91 | 33-37 |
| Mo | 10 | 9.93 | 9.7 | 9.47 | 9-10.5 |
| Co | balance | balance | balance | balance | balance |

Microscopic Inspection for Microcleanliness of the Alloy

The microscopic inspection for microcleanliness of the inventive alloy (example 1 and example 1a with an Ag core) and of the comparative alloy (example 2 and example 2a with an Ag core) was carried out according to the procedure and test method described above. Of 4 rods with an outer diameter of 31.75 mm, 5 transverse and 5 longitudinal sections were taken according to table 1 and metallographically prepared. The sections included a continuous plane from two surface locations and through the approximated center of the bar. The metallographically prepared sections were examined in the as-polished condition by scanning electron microscopy (SEM) using backscattered electron imaging (BEI). In BEI, the brightness of sample features is proportional to the atomic weight of the elements constituting those features. Thus, in BEI, present inclusions consisting of heavier elements than the surrounding matrix material appear brighter than the matrix material. Inclusions consisting of lighter elements than the surrounding matrix material appear darker than the matrix material. Since nonmetallic inclusions (for example, oxide or nitride inclusions) consist of lighter elements than the alloys of example 1 and example 2, in BEI these ceramic inclusions appear darker than the surrounding matrix material. Images were acquired at a magnification of 500× along a diametric line extending across the entire bar. Analysis of features darker and brighter than the background was conducted on the images using image analysis software to determine the maximum dimension for each detected feature. The largest dimension and area were recorded for each individual feature. The inclusions were categorized by largest dimension into 1 μm groups up to 14 μm. The total area of the dark and bright features was also calculated. Inclusions greater than 14 μm were also counted. Features smaller than 3.0 μm were not included in the measurements.

For each section, forty-eight fields of view were evaluated. For each direction, longitudinal and transverse, 480 images with a total area of 22.6 $mm^2$ were evaluated. The samples contained features that appeared darker and brighter than the bulk material using backscattered electron imaging. The darker features have a lower mean atomic number than the background and the brighter features have a higher mean atomic number than the background.

Results of the inclusion analysis of example 1 are illustrated in tables 4-6. Results of the inclusion analysis of example 2 are illustrated in tables 7-10. Image fields showing typical dark (ceramic) inclusions are illustrated in FIGS. 4, 5, 7-10.

Alloy of One Embodiment (Example 1)

TABLE 4

FEATURE COUNT TOTALS/EXAMPLE 1

| Largest Dimension | Number of Features | | | |
|---|---|---|---|---|
| | Longitudinal | | Transverse | |
| [μm] | Dark | Bright | Dark | Bright |
| 3.0-3.9 | 15 | 0 | 14 | 0 |
| 4.0-4.9 | 4 | 0 | 2 | 0 |
| 5.0-5.9 | 2 | 0 | 1 | 0 |
| 6.0-6.9 | 0 | 0 | 0 | 0 |
| 7.0-7.9 | 0 | 0 | 0 | 0 |
| 8.0-8.9 | 0 | 0 | 0 | 0 |
| 9.0-9.9 | 0 | 0 | 0 | 0 |
| 10.0-10.9 | 0 | 0 | 0 | 0 |
| 11.0-11.9 | 0 | 0 | 0 | 0 |
| 12.0-12.9 | 0 | 0 | 0 | 0 |
| 13.0-13.9 | 0 | 0 | 0 | 0 |
| 14.0-14.9 | 0 | 0 | 0 | 0 |
| >14.9 | 0 | 0 | 0 | 0 |
| Total | 21 | 0 | 17 | 0 |

TABLE 5

TOTAL INCLUSION AREA MEASUREMENTS FOR EXAMPLE 1

| | Area of Inclusions >3 μm in Length for Examination Region | | | | | |
|---|---|---|---|---|---|---|
| | Darker | | Brighter | | All | |
| Sample | Total [$μm^2$] | Percent of Total Area [%] | Total [$μm^2$] | Percent of Total Area [%] | Total [$μm^2$] | Percent of Total Area [%] |
| Longitudinal | 121 | 0.0006 | 0 | 0.0000 | 121 | 0.0006 |
| Transverse | 97 | 0.0005 | 0 | 0.0000 | 97 | 0.0005 |

TABLE 6

LONGEST DARK FEATURES FOR EXAMPLE 1

| | Feature Dimensions, [μm] | | |
|---|---|---|---|
| Number | Length | Breadth | Direction |
| 1 | 5.6 | 3.0 | Longitudinal |
| 2 | 5.4 | 3.7 | Longitudinal |
| 3 | 5.4 | 2.9 | Longitudinal |
| 4 | 4.9 | 2.2 | Longitudinal |
| 5 | 4.7 | 3.6 | Longitudinal |
| 6 | 4.6 | 1.9 | Longitudinal |
| 7 | 4.5 | 2.7 | Longitudinal |
| 8 | 4.5 | 2.4 | Longitudinal |
| 9 | 4.1 | 2.4 | Longitudinal |
| 10 | 3.9 | 3.0 | Longitudinal |

Example 2 (Comparative)

TABLE 7

FEATURE COUNT TOTALS/BARS 1-10/ALL SAMPLES

| Largest Dimension [μm] | Number of Features | | | |
|---|---|---|---|---|
| | Longitudinal | | Transverse | |
| | Dark | Bright | Dark | Bright |
| 3.0-3.9 | 25 | 21 | 6 | 46 |
| 4.0-4.9 | 19 | 7 | 3 | 11 |
| 5.0-5.9 | 7 | 1 | 1 | 1 |
| 6.0-6.9 | 6 | — | — | 1 |
| 7.0-7.9 | 7 | — | — | — |
| 8.0-8.9 | 4 | — | — | — |
| 9.0-9.9 | 1 | — | — | — |
| 10.0-10.9 | 2 | — | — | — |
| 11.0-11.9 | 2 | — | — | — |
| 12.0-12.9 | — | — | — | — |
| 13.0-13.9 | — | — | — | — |
| 14.0-14.9 | — | — | — | — |
| >14.9 | 4 | — | — | — |
| Total | 77 | 29 | 10 | 59 |

TABLE 8

TOTAL INCLUSION AREA MEASUREMENTS FOR EXAMPLE 2

| | Area of Inclusions >3 μm in Length for Examination Region | | | | | |
|---|---|---|---|---|---|---|
| | Darker | | Brighter | | All | |
| Sample | Total [μm²] | Percent of Total Area [%] | Total [μm²] | Percent of Total Area [%] | Total [μm²] | Percent of Total Area [%] |
| Longitudinal | 409 | 0.0018 | 75 | 0.0003 | 484 | 0.0021 |
| Transverse | 69 | 0.0003 | 152 | 0.0007 | 221 | 0.0010 |

TABLE 9

LONGEST DARK FEATURES FOR EXAMPLE 2

| | Feature Dimensions, [μm] | | |
|---|---|---|---|
| Number | Length | Breadth | Direction |
| 1 | 33.4 | 1.9 | Longitudinal |
| 2 | 18.9 | 1.6 | Longitudinal |
| 3 | 17.8 | 2.3 | Longitudinal |
| 4 | 15.4 | 1.4 | Longitudinal |
| 5 | 11.8 | 1.0 | Longitudinal |
| 6 | 11.1 | 1.1 | Longitudinal |
| 7 | 10.6 | 1.0 | Longitudinal |
| 8 | 10.3 | 1.8 | Longitudinal |
| 9 | 9.5 | 1.5 | Longitudinal |
| 10 | 8.9 | 2.2 | Longitudinal |

TABLE 10

LONGEST BRIGHT FEATURES FOR EXAMPLE 2

| | Feature Dimensions, [μm] | | |
|---|---|---|---|
| Number | Length | Breadth | Direction |
| 1 | 6.0 | 1.6 | Transverse |
| 2 | 5.6 | 2.8 | Longitudinal |
| 3 | 5.1 | 1.8 | Transverse |
| 4 | 4.9 | 2.3 | Transverse |
| 5 | 1.9 | 1.8 | Transverse |
| 6 | 1.0 | 1.8 | Longitudinal |
| 7 | 4.6 | 1.3 | Transverse |
| 8 | 4.5 | 1.2 | Transverse |
| 9 | 4.4 | 1.6 | Longitudinal |
| 10 | 4.4 | 0.9 | Transverse |

According to Table 8 of example 2 (comparative), the total area of dark inclusions found is 478 μm² (409 μm² in longitudinal direction and 69 μm² in transverse direction). According to Table 5 of example 1 (inventive), the total area of dark inclusions found is only 218 μm² (121 μm² in longitudinal direction and 97 μm² in transverse direction). So the amount of dark inclusions (Percent of total area) in example 1 (inventive) is only 4.8 ppm (0.00048%) while in example 2 (comparative) the amount of dark inclusions is 11 ppm (0.0011%). In terms of inclusions (micro-cleanliness) this means that example 1 (inventive) is more than 2 times cleaner than example 2 (comparative).

Fatigue Test Results

Two lots of wire of example 1 (dia. 102 μm) were tested against two lots of wire or example 2 (same diameter—102 μm) having comparable mechanical properties (UTS of 1862-1875 MPa).

TABLE 11

| | Example 1 (inventive) | | Example 2 (comparative) | |
|---|---|---|---|---|
| Material | | | Lot C | |
| Batch | Lot A | Lot B | (FIG. 5 & 6) | Lot D |
| UTS [MPa] | 1870 | 1875 | 1862 | 1871 |
| YM [GPa] | 190 | 191 | 190 | 190 |
| Elongation [%] | 2.8 | 2.9 | 2.7 | 2.8 |

At an applied stress of 700 MPa, the wire of all four lots reached the fatigue endurance limit, which means the wire does not fail and tests are stopped after 100 Million cycles. While the wire of example 1 showed no outliers at 700 MPa and below, 4 samples of example 2 failed at less than 2.7 Million cycles and two other samples ran 40-50 Million cycles. All other samples tested at an applied stress of 700 MPa and below survived 100 Million cycles without rupture. For Example 2 wire lot C, sample C25 tested at an applied stress of 700 MPa broke after only 71,790 cycles and sample C31 tested at an applied stress of 520 MPa broke after only 145,260 cycles. Sample C26 tested at an applied stress of 700 MPa broke after 47,547,540 cycles and sample C29 tested at an applied stress of 700 MPa broke after 41,282,990 cycles. For example 2 wire lot D, sample D27 tested at an applied stress of 700 MPa broke after only 549,227 cycles and sample D35 tested at an applied stress of 520 MPa broke after only 2,689,952 cycles.

SEM-images of sample C25 illustrates an inclusion at the fracture surface. In EDX analysis, high peaks for Aluminium, Magnesium, Chromium and Oxygen were found. This mixed-oxide inclusion was identified as the crack initiation point for the early failure of this sample. An SEM-image of sample D35 also illustrates an inclusion at the fracture surface. Again, in EDX analysis, high peaks for Aluminium, Magnesium, Chromium and Oxygen were found. Also this mixed-oxide inclusion can be identified as the crack initiation point for the early failure of this sample. SEM investigations of samples C31 and D27 also showed oxide-inclusions at the fracture surface which were identified causing the early failure. For both samples, the same elements (Aluminium, Magnesium, Chromium, Oxygen) illustrate high peaks in EDX analysis for these two samples.

TABLE 12

| stress level [MPa] | Example 1 (inventive) (Lot A) No. of cycles | Example 1 (inventive) (Lot B) No. of cycles | Example 2 (comparative) (Lot C) No. of cycles | Example 2 (comparative) (Lot D) No. of cycles |
|---|---|---|---|---|
| 1430 | 21092 | 66720 | 20700 | 35130 |
| 1430 | 12740 | 63781 | 22140 | 57120 |
| 1430 | 28919 | 59140 | 36120 | 32460 |
| 1430 | 19334 | 37942 | 23550 | 35010 |
| 1430 | 18119 | 39178 | 18270 | 28996 |
| 1430 | 21983 | 22380 | 18150 | 33313 |
| 1040 | 38670 | 128644 | 136680 | 149971 |
| 1040 | 58474 | 218106 | 1004289 | 308580 |
| 1040 | 46980 | 194108 | 8656363 | 80766 |
| 1040 | 34806 | 41310 | 107640 | 178770 |
| 1040 | 38045 | 539089 | 7856526 | 74323 |
| 1040 | 39120 | 290101 | 6852041 | 127650 |
| 880 | 5888420 | 4715690 | 39485962 | 72523366 |
| 880 | 4233055 | 5816670 | 102020453 | 100000000 |
| 880 | 6324748 | 2144125 | 100800000 | 6171230 |
| 880 | 13571905 | 2068519 | 114000000 | 4407264 |
| 880 | 8824316 | 1725656 | 101000000 | 102000000 |
| 880 | 7680042 | 1815390 | 100000000 | 57462763 |
| 800 | 104700000 | 40051186 | — | — |
| 800 | 96874223 | 16938278 | — | — |
| 800 | 59716187 | 26518613 | — | — |
| 800 | 54411683 | 79084889 | — | — |
| 800 | 64971417 | 46467823 | — | — |
| 800 | 100000000 | 24231864 | — | — |
| 700 | 103000000 | 105000000 | 71790 | 100000000 |
| 700 | 109852488 | 97119288 | 47547540 | 100000000 |
| 700 | 101589761 | 107000000 | 100000000 | 549227 |
| 700 | 101623566 | 104000000 | 100000000 | 101337563 |
| 700 | 102000000 | 101000000 | 41282990 | 100000000 |
| 700 | 103000000 | 103000000 | 100000000 | 100000000 |
| 520 | 100000000 | 100000000 | 145260 | 100000000 |
| 520 | 118987000 | 106000000 | 110800000 | 110800000 |
| 520 | 102064330 | 102000000 | 101000000 | 101000000 |
| 520 | 100963860 | 100613526 | 100500000 | 100500000 |
| 520 | 100845911 | 100845911 | 108000000 | 2689952 |
| 520 | 101009712 | 101006089 | 100000000 | 112000000 |

These fatigue test results are plotted in FIG. 12. As can be seen from this plot, lots C and D (comparative) illustrate significantly more undesired outliers than for lots A and B (inventive).

Three lots of example 1a/Ag28% wire (diameter 127 μm) were also tested against three lots of example 2a wire (same diameter—127 μm). All six wire lots have comparable mechanical properties (UTS of 1456-1475 MPa).

TABLE 13

| | Example 1a + 28 weight % Ag (inventive) | | | Example 2a + 28 weight % As (comparative) | | |
|---|---|---|---|---|---|---|
| Batch | Lot E | Lot F | Lot G | Lot H | Lot J (FIG. 10 & 11) | Lot K |
| UTS [MPa] | 1456 | 1469 | 1474 | 1460 | 1462 | 1475 |
| YM [GPa] | 121 | 121 | 122 | 121 | 122 | 122 |
| Elongation [%] | 2.2 | 2.3 | 2.3 | 2.1 | 2.0 | 2.3 |

At an applied stress of 414 MPa, the wire of all four lots reached the fatigue endurance limit, means the wire does not fail and tests are stopped after 100 Million cycles. While example 1a/Ag28% wire illustrated no outliers at 414 MPa and below, 4 samples of example 2a/Ag28% wire failed at less than 1.4 Million cycles. All other samples tested at an applied stress of 414 MPa and below survived 100 Million cycles without rupture. For example 2a/Ag28% wire lot H, sample H24 tested at an applied stress of 414 MPa broke after only 1,041,679 cycles. Sample J18 tested at an applied stress of 518 MPa broke after 588,028 cycles and sample J23 tested at an applied stress of 414 MPa broke after 263,488 cycles. Sample K24 tested at an applied stress of 414 MPa broke after 1,355,189 cycles. As an example, SEM-images of sample J23 illustrate an inclusion at the fracture surface. In EDX analysis, high peaks for Aluminium, Magnesium, Chromium and Oxygen were found. This mixed-oxide inclusion was identified as the crack initiation point for the early failure of this sample. SEM investigations of samples H24, J18 and K24 also showed oxide-inclusions at the fracture surface which were identified causing the early failure. For all three samples, the same elements (Aluminium, Magnesium, Chromium, Oxygen) illustrate high peaks in EDX analysis for these three samples.

TABLE 14

| | Example 1a + 28 weight % Ag | | | Example 2a + 28 weight % Ag | | |
|---|---|---|---|---|---|---|
| stress level [MPa] | lot E No. of cycles | lot F No. of cycles | lot G No. of cycles | lot H No. of cycles | lot J No. of cycles | lot K No. of cycles |
| 969 | 31,887 | 33,065 | 21,487 | 47,982 | 38,148 | 32,926 |
| 969 | 29,321 | 28,116 | 23,461 | 43,661 | 41,085 | 20,818 |
| 969 | 32,555 | 29,941 | 28,763 | 30,298 | 33,187 | 32,299 |
| 969 | 26,918 | 23,418 | 18,464 | 37,888 | 36,247 | 38,901 |
| 969 | 22,089 | 30,467 | 20,198 | 43,092 | 41,944 | 42,978 |
| 725 | 246,766 | 231,412 | 114,746 | 74,414 | 235,494 | 109,597 |
| 725 | 199,054 | 189,441 | 123,746 | 79,498 | 128,377 | 92,419 |
| 725 | 287,665 | 262,994 | 168,374 | 94,638 | 118,922 | 91,877 |

TABLE 14-continued

|  | Example 1a + 28 weight % Ag | | | Example 2a + 28 weight % Ag | | |
|---|---|---|---|---|---|---|
| stress level [MPa] | lot E No. of cycles | lot F No. of cycles | lot G No. of cycles | lot H No. of cycles | lot J No. of cycles | lot K No. of cycles |
| 725 | 200,822 | 186,242 | 145,355 | 75,062 | 162,522 | 102,834 |
| 725 | 500,045 | 290,377 | 169,176 | 62,082 | 238,611 | 99,864 |
| 580 | 1,405,296 | 1,612,743 | 979,651 | 409,644 | 6,780,968 | 311,974 |
| 580 | 1,077,510 | 1,131,168 | 1,846,396 | 668,132 | 12,545,505 | 8,369,715 |
| 580 | 8,201,513 | 993,416 | 1,684,673 | 1,031,447 | 1,945,002 | 3,001,478 |
| 580 | 2,511,763 | 2,197,173 | 639,464 | 342,282 | 2,639,912 | 219,634 |
| 580 | 841,436 | 884,196 | 2,076,465 | 3,539,353 | 8,566,249 | 2,009,899 |
| 518 | 40,051,186 | 86,414,732 | 71,763,385 | 100,000,000 | 100,000,000 | 100,000,000 |
| 518 | 100,000,000 | 78,411,674 | 83,944,821 | 100,000,000 | 100,000,000 | 100,000,000 |
| 518 | 79,084,889 | 100,000,000 | 35,946,337 | 100,000,000 | 588,028 | 100,000,000 |
| 518 | 46,467,823 | 100,000,000 | 100,000,000 | 100,000,000 | 100,000,000 | 100,000,000 |
| 518 | 100,000,000 | 87,867,423 | 54,676,179 | 100,000,000 | 100,000,000 | 100,000,000 |
| 414 | 100,000,000 | 100,000,000 | 100,000,000 | 100,000,000 | 100,000,000 | 100,000,000 |
| 414 | 100,000,000 | 100,000,000 | 100,000,000 | 100,000,000 | 100,000,000 | 100,000,000 |
| 414 | 100,000,000 | 100,000,000 | 98,674,345 | 100,000,000 | 263,488 | 100,000,000 |
| 414 | 100,000,000 | 100,000,000 | 100,000,000 | 1,041,679 | 100,000,000 | 1,355,189 |
| 414 | 100,000,000 | 100,000,000 | 96,674,523 | 100,000,000 | 100,000,000 | 100,000,000 |
| 329 | 100,000,000 | 100,000,000 | 100,000,000 | — | — | — |
| 329 | 100,000,000 | 100,000,000 | 100,000,000 | — | — | — |
| 329 | 100,000,000 | 100,000,000 | 100,000,000 | — | — | — |
| 329 | 100,000,000 | 100,000,000 | 100,000,000 | — | — | — |
| 329 | 100,000,000 | 100,000,000 | 100,000,000 | — | — | — |

These fatigue test results are plotted in FIG. 13. As can be seen from this plot, lots H, J and K (comparative) illustrate significantly more undesired outliers than for lots E, F and G (inventive).

Pacemaker Lead

A wire with thickness 25 µm was prepared according to the method described above and with compositions of the alloy as given in table 3. The wires were arranged into a lead as described in FIG. 1. The leads were tested for fatigue resistance and for impurity inclusions. The results are illustrated in table 15.

TABLE 15

| Example | Fatigue resistance | Purity from inclusions |
|---|---|---|
| Heat 1 | ++ | ++ |
| Heat 2 | ++ | ++ |
| Heat 3 | ++ | ++ |
| Commercial heat | − | − |

++ = very good,
− = poor

What is claimed is:

1. An alloy comprising:
   about 10 to about 30 weight % Cr;
   about 20 to about 50 weight % Ni;
   about 2 to about 20 weight % Mo;
   about 10 to about 50 weight % Co; and
   less than about 0.01 weight % Al;
   wherein each weight % is based on the total weight of the alloy.

2. The alloy of claim 1 further comprising less than about 0.005 weight % Mg, based on the total weight of the alloy.

3. The alloy of claim 1 further comprising less than about 0.005 weight % Ca, based on the total weight of the alloy.

4. The alloy of claim 1 further comprising less than about 0.005 weight % Ce, based on the total weight of the alloy.

5. The alloy of claim 1 further comprising less than about 0.1 weight % Ti, based on the total weight of the alloy.

6. The alloy of claim 1 further comprising from about 0.0001 to about 1 weight % Fe.

7. The alloy of claim 1, wherein at least one of the following is satisfied:
   a) the content of C in the alloy is less than about 0.1 weight %;
   b) the content of B in the alloy is less than about 0.01 weight %;
   c) the content of P in the alloy is less than about 0.01 weight %;
   d) the content of S in the alloy is less than about 0.005 weight %;
   wherein each weight % is based on the total weight of the alloy.

8. The alloy of claim 1, wherein at least one of the following is satisfied:
   a) the content of Mn in the alloy is less than about 0.05 weight %;
   b) the content of Si in the alloy is less than about 0.05 weight %;
   wherein each weight % is based on the total weight of the alloy.

9. The alloy of claim 1, wherein at least one of the following is satisfied:
   a) the content of O in the alloy is in the range from about 0.0001 to about 0.05 weight %;
   b) the content of N in the alloy is in the range from about 0.0001 to about 0.01 weight %;
   wherein each weight % is based on the total weight of the alloy.

10. One of an electrical wire, a wire of a medical device, and a wire of a pacemaker device, comprising an alloy according to claim 1.

* * * * *